(12) United States Patent
Cho et al.

(10) Patent No.: US 8,703,740 B2
(45) Date of Patent: Apr. 22, 2014

(54) COMPOSITION FOR PREVENTING ADHESION

(75) Inventors: Il Hwan Cho, Gyeonggi-do (KR); Sei Kwang Hahn, Gyeongsangbuk-do (KR); Eui Jin Hwang, Gyeonggi-do (KR); Jang Sik Shin, Gyeonggi-do (KR); Junseok Yeom, Gyeongsangnam-do (KR)

(73) Assignees: Shin Poong Pharmaceutical Co., Ltd., Gyeonggi-Do (KR); Postech Academy-Industry Foundation, Gyeongsangbuk-Do (KR)

( * ) Notice: Subject to any disclaimer, the term of this patent is extended or adjusted under 35 U.S.C. 154(b) by 0 days.

(21) Appl. No.: 13/131,996

(22) PCT Filed: Nov. 25, 2009

(86) PCT No.: PCT/KR2009/006962
§ 371 (c)(1),
(2), (4) Date: May 31, 2011

(87) PCT Pub. No.: WO2010/064806
PCT Pub. Date: Jun. 10, 2010

(65) Prior Publication Data
US 2011/0237542 A1    Sep. 29, 2011

(30) Foreign Application Priority Data
Dec. 1, 2008  (KR) .................. 10-2008-0120346

(51) Int. Cl.
*A61K 31/728* (2006.01)

(52) U.S. Cl.
USPC ......................................................... 514/60

(58) Field of Classification Search
USPC .................................................... 514/55, 60
See application file for complete search history.

(56) References Cited

U.S. PATENT DOCUMENTS

| | | | |
|---|---|---|---|
| 4,141,973 A | 2/1979 | Balazs | |
| 5,358,973 A | 10/1994 | Lindblad et al. | |
| 5,704,297 A * | 1/1998 | Hussain et al. | 106/215.5 |
| 5,891,460 A | 4/1999 | Rodgers et al. | |
| 6,387,413 B1 | 5/2002 | Miyata et al. | |
| 6,534,693 B2 | 3/2003 | Fischell et al. | |
| 6,548,081 B2 | 4/2003 | Sadozai et al. | |
| 6,638,538 B1 * | 10/2003 | Hashimoto et al. | 424/548 |
| 7,834,065 B2 | 11/2010 | Nakajima et al. | |
| 8,133,504 B2 | 3/2012 | Kettlewell et al. | |
| 2002/0055701 A1 | 5/2002 | Fischell et al. | |
| 2002/0071855 A1 | 6/2002 | Sadozai et al. | |
| 2003/0104039 A1 | 6/2003 | Berthold et al. | |
| 2003/0152609 A1 | 8/2003 | Fischell et al. | |
| 2004/0006296 A1 | 1/2004 | Fischell et al. | |
| 2004/0018228 A1 | 1/2004 | Fischell et al. | |
| 2004/0071756 A1 | 4/2004 | Fischell et al. | |
| 2004/0241211 A9 | 12/2004 | Fischell et al. | |
| 2005/0084514 A1 | 4/2005 | Shebuski et al. | |
| 2005/0281860 A1 | 12/2005 | Fischell et al. | |
| 2006/0127387 A1 * | 6/2006 | Zikria et al. | 424/94.4 |
| 2006/0286063 A1 | 12/2006 | Shebuski et al. | |
| 2007/0110796 A1 | 5/2007 | Fischell et al. | |
| 2007/0282014 A1 | 12/2007 | Boll et al. | |
| 2008/0058469 A1 | 3/2008 | Abe et al. | |
| 2009/0062233 A1 | 3/2009 | Ji et al. | |
| 2009/0098061 A1 | 4/2009 | Suzuki et al. | |
| 2009/0238875 A1 | 9/2009 | Noh et al. | |

FOREIGN PATENT DOCUMENTS

| | | |
|---|---|---|
| CN | 101193645 | 6/2008 |
| EP | 1593394 | 11/2005 |
| EP | 1905443 A1 | 6/2006 |
| JP | 1993-331053 | 12/1993 |
| JP | 11-246301 | 9/1999 |
| JP | 2000-116765 | 4/2000 |
| JP | 2008-508916 | 3/2008 |
| JP | 2011-509932 | 3/2011 |
| KR | 10-0019054 | 2/2008 |
| KR | 10-0849185 | 7/2008 |
| WO | 2004/020473 | 3/2004 |
| WO | 2004/022603 | 3/2004 |
| WO | 2005/08942 | 9/2005 |
| WO | 2005-087289 | 9/2005 |

(Continued)

OTHER PUBLICATIONS

Kim S-K and Rajapakse N. Enzymatic production and biological activities of chitosan oligosaccharide (COS): A review. Carbohydrate Polymers 62:357-368, 2005.*

(Continued)

*Primary Examiner* — Wu-Cheng Winston Shen
*Assistant Examiner* — Yih-Horng Shiao
(74) *Attorney, Agent, or Firm* — Greenblum & Bernstein, P.L.C.

(57) ABSTRACT

The present invention relates to a composition for preventing tissue adhesion which comprising a bio-compatible hyaluronic acid and a polymer compound. More specifically, the invention is a composition containing hyaluronic acid which has not been modified by a chemical crosslinking or other chemical modification a method for preparing the same, and a composition for adhesion prevention with superior efficacy. The composition of the present invention for preventing adhesion exhibits a physical barrier function and a new adhesion prevention function whereby thrombus formation, which is the basis of adhesion, is inhibited. Unlike conventional compositions which simply mix polymeric substances that function as physical barriers, the present invention performs a more effective role as a physical barrier by undergoing decomposition, absorption and excretion after a certain period inside a human body, does not interfere with healing of scars following surgery, and exhibits superior effects since application to areas of surgery is convenient.

22 Claims, 5 Drawing Sheets

(56) References Cited

FOREIGN PATENT DOCUMENTS

| WO | 2006-080523 | 8/2006 |
| WO | 2006/132310 | 12/2006 |
| WO | 2007/083870 | 7/2007 |

OTHER PUBLICATIONS

Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
Schnuringer et al. Prevention of postoperative peritoneal adhesion: a review of the literature. Am J Surg 201:111-121, 2011.*
Feldschuh et al. Prediction of normal blood volume: Relation of blood volume to body habitus. Circulation 56:605-612, 1977.*
Kenner T. The measurement of blood density and its meaning. Basic Res Cardiol 84:111-124, 1989.*
European Search Report issued with respect to counterpart European Application No. 09830544.4, dated May 18, 2012.
Australian Office Action issued with respect to counterpart Australian Application No. 2009323210, dated May 16, 2012.
Gist R S et al., "Use of sodium hetastarch (Hespan) solution for reduction of postoperative adhesion formation in rabbits." Journal of Investigative Surgery : The Official Journal of the Academy of Surgical Research Sep.-Oct. 1996 LNKD-PUBMED:8951660, vol. 9, No. 5, XP009159085, pp. 369-373.
Menzies, Ann. Royal Coll. Surg. Engl., 75, 1993, pp. 147-153.
Risberg, Eur. J. Surg., Suppl 577, 1997, pp. 32-39.
Grainger, Infert. Reprod. Med. Oin. North Am., 5:3, 1994, pp. 391-404.
Bhatia et al., Am. Surg., 63, 1983, pp. 775-777.
Franz et al., Anesth. Analg., 92, 2001, pp. 1402-1407.
Luciano et al., Am., J. Obstet. Gynecol., 146, 1983, pp. 88-92.
Korean Office Action in 10-2008-0120346.
International Search Report for PCT/KR2009/006962 in Korean and English.
English translation of Chinese Office Action issued with respect to counterpart Chinese Application No. 200980148062.4, dated Jul. 6, 2012.

* cited by examiner

COMPOSITION FOR PREVENTING ADHESION

TECHNICAL FIELD

The present invention relates to a composition for preventing adhesion including a bio-compatible hyaluronic acid and a polymer compound. More specifically, the present invention relates to a composition for preventing adhesion with superior efficacy and including a hyaluronic acid that has not been modified by a chemical crosslinking agent or chemical modifying agent, and a method for preparing the same.

BACKGROUND ART

Adhesions are attachments between the surrounding organs or tissues that are normally separate from one another, resulting from excessive generation of fibrous tissues or extravasation and clotting of blood during healing of wounds including traumas caused by inflammation, cut, chafing, surgery or the like. Adhesions may arise after any kind of surgical operations and may cause serious clinical sequelas due to attachments between organs or tissues around the surgical regions, during post-operative healing.

Generally, the incidence of post-operative organ adhesions is reportedly in a range of 55% to 93% (*Ann. Royal Coll. Surg. Engl.*, 75, 147-153, 1993). A large percentage of abdominal surgeries result in adhesions. Although some of these adhesions may undergo spontaneous decomposition, adhesions still remain in most cases even after healing of wounds, which may result in a variety of sequelas. The kind of sequelas is very various. According to the US statistical data, it is known that post-operative adhesions entails, as main symptoms, 49% to 74% of enterocleisis, 15% to 20% of infertility, 20% to 50% of chronic pelvic pain, and 19% of enterobrosia in a subsequent surgery (*Eur. J. Surg.*, Suppl 577, 32-39, 1997).

The mechanism of intraperitoneal adhesion formation is specifically described in the paper published by Granger (*Infert. Reprod. Med. Clin. North Am.*, 5:3, 391-404, 1994). According to Granger, adhesions are initiated by fibrin resulting from the clotting process of blood among exudates generated after surgeries. The inflammatory exudate is rich in fibrin which forms a clot of blood on wound surfaces. As fibrin is degraded, mesothelium is regenerated, which normally results in healing of wounds. The decomposition of fibrin or fibrinolysis is dependent on the conversion of plasminogen to plasmin which is a fibrinolytic enzyme, and this reaction is promoted by a tissue plasminogen activator (tPA) existing in the mesothelium and the underlying stroma. However, if fibrinolysis does not occur, inflammatory cells and fibroblasts infiltrate into the fibrin matrix to result in organized adhesions. In this manner, adhesions take place through a series of the fibrinogenesis mechanism and the fibrinolysis mechanism, and the relationship between both mechanisms is not simple and is closely related to the healing process of wounds.

As one of various methods for preventing such adhesions, intensive research has been focused on an anti-adhesion agent that prevents the formation of adhesions between the adjacent tissues, through the formation of a physical barrier during healing of wounds of tissues using a barrier, as similarly in the action of a surfactant. The anti-adhesion barriers used for these barriers may be broadly divided into two classes in view of their types: one is a membrane type barrier including a film type, a non-woven type and a sponge type, and the other is a solution type barrier including a gel type.

Examples of the membrane type anti-adhesion material include oxidized-regenerated cellulose, expanded polytetrafluoroethylene (hereinafter, referred to as "ePTFE"), films made up of modified hyaluronic acid, sodium carboxymethyl cellulose and chemical modifying agents, and the like.

Examples of the solution type anti-adhesion material include a lactated Ringer's solution, a dextran-70 solution, a heparin solution, a sodium carboxymethyl cellulose solution, a hyaluronic acid solution, a chondroitin sulfate solution, a polyethylene glycol solution, a poloxamer solution, and the like. Among these solution type anti-adhesion materials, a lactated Ringer's solution, a dextran-70 solution, a heparin solution and the like have a main mechanism which, during healing of the peritoneum, induces fibrin-covered surfaces to move away from each other. Although they are preparations which have been used to inhibit adhesions by separating tissues from each other, satisfactory anti-adhesion effects are not achieved due to their rapid absorption into the peritoneum (*Am. Surg.*, 63, 775-777, 1983). Meanwhile, since polyethylene glycol and the like are not degraded in vivo, only a low-molecular weight material that can be discharged through a metabolic pathway when absorbed can be used. However, the use of such a low-molecular weight material results in excessively rapid absorption, so that it cannot serve as an effective barrier to prevent adhesions for an extended period of time.

Meanwhile, hyaluronic acid disclosed in U.S. Pat. No. 4,141,973 is a linear macromolecular polysaccharide consisting of alternately bonded $\beta$-D-N-acetylglucosamine and $\beta$-D-glucuronic acid and is known to exhibit excellent biocompatibility even when it is transplanted or infused in vivo. However, also due to in vivo decomposition and absorption within a relatively short period of time, there is a limitation in terms of performance as an anti-adhesion agent.

As an attempt to improve such disadvantages, U.S. Pat. No. 6,387,413 B1 discloses a preparation of a hyaluronic acid gel composition by adding a polymer compound such as carboxymethyl cellulose, for the purpose of supplementing properties of hyaluronic acid gel in terms of physical properties.

As described above, a variety of investigations has been made to supplement properties of hyaluronic acid gel in terms of physical properties. Among others, in order to improve disadvantages of hyaluronic acid in terms of being readily water-soluble upon in vivo applications and relatively short in vivo retention time, various modifications of hyaluronic acid have been proposed which is modified by a variety of chemical crosslinking agents or chemical modifying agents.

Although the materials thus developed up to date present potentialities for the prevention of adhesions, since chemical crosslinking methods are largely employed, there are problems associated with inconveniences of removing crosslinking agents or additives and complicated processes in conjunction with problems of toxicity and safety.

As a result of a variety of extensive and intensive studies and experiments to solve the problems as described above, that is, problems associated with low efficiency of anti-adhesion function, synthesis of chemical crosslinking agents or additives, and possible residual toxicity, the inventors of the present invention discovered that it is possible to solve the above-described problems by providing a composition including a high-molecular weight hyaluronic acid with optimized biocompatibility without the use of a chemical crosslinking agent. The present invention has been completed based on these findings.

Further, unlike conventional products including a simple mixture of polymeric materials that serve as physical barriers in terms of anti-adhesion effects, the present invention is based on a new functional approach of adhesion prevention wherein the use of hyaluronic acid and hydroxyethyl starch in the present invention not only functions as a physical barrier, but also inhibits thrombus formation which is basically responsible for the incidence of adhesions. Therefore, the present invention can be distinguished from conventional products and is also confirmed to be excellent in terms of anti-adhesion effects and safety.

DISCLOSURE OF THE INVENTION

Technical Problem

Therefore, the present invention is intended to provide a composition for prevention adhesion including a hyaluronic acid and a hydroxyethyl starch or chitooligosaccharide. The composition is preferably a gel type composition.

Further, the present invention is intended to provide use of a composition including a hyaluronic acid and a hydroxyethyl starch or chitooligosaccharide, for manufacturing a medicinal preparation for preventing adhesion.

Further, the present invention is intended to provide a method for preventing a post-operative adhesion, including administering a composition including a hyaluronic acid and a hydroxyethyl starch or chitooligosaccharide to a mammal including a human.

Further, the present invention is based on a new functional approach of adhesion prevention wherein a composition including a hyaluronic acid and a hydroxyethyl starch provided by the present invention not only functions as a physical barrier, but also inhibits thrombus formation which is the basis for the incidence of adhesions and therefore can be distinguished from conventional products and provides excellent effects also in terms of anti-adhesion effects and safety.

Further, the present invention reduces the incidence of adhesions by delaying early decompostion and absorption of hyaluronic acid in vivo as exhibited upon single use of hyaluronic acid, through the provision of a composition including a hyaluronic acid and a chitooligosaccharide.

Further, the present invention is intended to provide a composition which reduces occurrences of post-operative adhesions, prevents the formation of adhesions after primary surgeries, and when healing of wounds is completed, is capable of being decomposed and absorbed in vivo and then discharged.

Technical Solution

The composition of the present invention is obtained by adding a polymeric material to hyaluronic acid. Although the polymeric material may be preferably hydroxyethyl starch or water-soluble chitooligosaccharide, any polymeric material may be used including PLGA (poly(DL-lactide-co-glycolide)), PLL (poly-L-lysine), PEG (polyethylene glycol), HEC (hydroxyethyl cellulose), CMC (carboxymethyl cellulose) and the like, as long as it is capable of supplementing inherent properties of hyaluronic acid gel with respect to the required physical properties of medicinal materials which are not readily satisfied by a single use of the hyaluronic acid gel.

Therefore, the present invention provides a composition for preventing adhesion including a hyaluronic acid and a hydroxyethyl starch or water-soluble chitooligosaccharide. The composition is preferably a gel type composition.

Further, the present invention provides use of a composition including a hyaluronic acid and a hydroxyethyl starch or chitooligosaccharide, for manufacturing a medicinal preparation for preventing adhesion.

Further, the present invention provides a method for preventing a post-operative adhesion of surrounding organs or tissues, including administering a composition including a hyaluronic acid and a hydroxyethyl starch or chitooligosaccharide to a mammal including a human.

Hereinafter, the composition for preventing adhesion in accordance with the present invention will be described in more detail.

1. Hyaluronic Acid (Hereinafter, Referred to as "HA")

As the hyaluronic acid in accordance with the present invention, any one extracted from animal tissues or prepared by a fermentation method may be used irrespective of its origins. Hyaluronic acid is decomposed by hyaluronidase, then absorbed and eliminated through a metabolic pathway.

Further, the hyaluronic acid in accordance with the present invention is a bio-derived material that has not been subjected to chemical crosslinking, and is free from toxicity accumulated in the human body due to a long-term in vivo retention which is the problem of conventional crosslinked hyaluronic acid and therefore is superior to conventional preparations in terms of safety.

The molecular weight of the hyaluronic acid in accordance with the present invention is in a range of about $5.0 \times 10^5$ to about $5.0 \times 10^6$ Da, and preferably a range of about $0.8 \times 10^6$ to about $3 \times 10^6$ Da. Hyaluronic acid having the above-specified range of a molecular weight has an appropriate in vivo half-life and therefore can serve as a physical barrier. On the other hand, conventional low-molecular weight hyaluronic acid (lower than $5.0 \times 10^5$) may have difficulty in being maintained as a physical barrier during healing of wounds. Hyaluron having a high molecular weight higher than $3 \times 10^6$ Da becomes very high in terms of viscosity, which may result in problems associated with production processes such as transfer, filtration, etc., thus being undesirable.

The content of the hyaluronic acid in accordance with the present invention is in a range of about 0.3 to about 7.0% by weight, and preferably about 0.5 to about 5.0% by weight, based on the total weight of the composition of the present invention. If the content of the hyaluronic acid is lower than 0.3% by weight, anti-adhesion effects may be limited. On the other hand, if the content of the hyaluronic acid is higher than 7.0% by weight, this may result in problems in terms of production due to viscosity.

2. Hydroxyethyl Starch (Hereinafter, Referred to as "HES")

In the composition in accordance with the present invention, HES is used as a pharmaceutical ingredient for lowering the occurrence of blood clotting in the blood clotting mechanism which is fundamentally responsible for the incidence of adhesion.

A variety of hydroxyethyl starches are currently used as colloidal blood volume substitute solutions. These hydroxyethyl starches are classified as hydroxyethyl groups and other parameters mainly depending on their molecular weight and/or their etherification. Representative examples thereof include hetastarch (HES 450/0.7) and pentastarch (PES 200/0.5).

HES is specified by a molecular weight usually abbreviated as KDa on the basis of weight average, a etherification or molar substitution degree MS for hydroxyethyl groups (for example, as 0.5 in HES 200/0.5; MS=average molar ratio of hydroxyethyl group to anhydrous glucose unit), or a substitution degree (for example, DS=ratio of mono- or polyhydroxyethylated glucose to total anhydrous glucose unit). HES under clinical applications may be classified into high molecular weight (450 kDa), medium molecular weight (200 kDa to 250 kDa) and low-molecular weight (70 kDa to 130 kDa) preparations, depending on their molecular weight.

HES have non-specific effects against blood clotting. These effects are caused by dilution of blood occurring during the infusion of HES into a circulation system. Such an influence on blood dilution may result in lowering of blood clotting in response to dilution of clotting factors. According to early research, it is mentioned that the molecular weight of HES has an effect on blood clotting. However, Franz et al have mentioned that blood clotting disorders exhibit no significant difference between high molecular weight and low molecular weight of HES (*Anesth. Analg.*, 92, 1402-1407, 2001), and European Patent No. 2005-050877 has mentioned that hemostatic inhibition of HES solutions is significantly influenced by a molar substitution degree rather than an average molecular weight. In terms of these mentions, it is considered that functions of blood platelets will be significantly influenced by other factors, not by the average molecular weight of HES.

Examples of HES solutions, which have received approval from FDA as a blood volume substitute solution and are currently commercially available abroad, include Hextend (HES 670/0.75, Biotime), Hespan (HES 130/0.4, BBraun), and Voluven (HES 130/0.4, Fresenius kabi).

The molecular weight of hydroxyethyl starch in accordance with the present invention is in a range of about $2.0 \times 10^5$ to about $1.0 \times 10^6$ Da, and preferably about $2.5 \times 10^5$ to about $6.7 \times 10^5$ Da. If the molecular weight of hydroxyethyl starch is lower than $2.0 \times 10^5$ Da, this may be not effective for the prevention of adhesions. On the other hand, if the molecular weight of hydroxyethyl starch is higher than $1.0 \times 10^6$, this may result in a problem of increasing an in vivo half-life. The molar substitution degree of hydroxyethyl starch used is in a range of about 0.2 to about 0.8, and preferably about 0.75 to about 0.4. If the molar substitution degree of hydroxyethyl starch is lower than 0.2, this may be not effective for the prevention of adhesions. On the other hand, if the molar substitution degree of hydroxyethyl starch is higher than 0.8, this may result in a problem associated with safety of the material itself.

Further, the content of the hydroxyethyl starch in accordance with the present invention is in a range of about 0.05 to about 3.0% by weight, and preferably about 0.1% by weight to about 2.0% by weight, based on the total weight of the composition in accordance with the present invention. If the content of the hydroxyethyl starch is lower than 0.05% by weight, this may be not effective for the prevention of adhesions. On the other hand, if the content of the hydroxyethyl starch is higher than 3.0% by weight, this may result in lowering of additive effects thereof and long-term in vivo retention thereof.

3. Chitooligosaccharide (Hereinafter, Referred to as "COS")

Chitin and chitosan are naturally-occurring polysaccharides and have recently attracted particular attention. Chitosan is a deacetylation product of chitin existing in nature (crab, shrimp, crustacean) and is a naturally-occurring macromolecular polysaccharide consisting of a polymer of β-1, 4-linked glucosamine. Due to having an excessively high molecular weight which consequently results in lowering of in vivo absorption rate or solubility, chitosan exhibits limitations of applications thereof despite excellent physiological activity.

On the other hand, chitooligosaccharide is a partial decomposition product of chitin and chitosan, and has a high solubility, a highly reactive primary amino group which enables various chemical modifications, a high in vivo absorptivity, and an antibacterial activity while having physiological properties of chitosan. Therefore, it was confirmed that chitooligosaccharide can contribute to the expression of anti-adhesion effects as a medical material.

The molecular weight of the chitooligosaccharide in accordance with the present invention is in a range of about $0.5 \times 10^3$ to about $1.0 \times 10^4$ Da, and preferably a range of about $1 \times 10^3$ to about $5 \times 10^3$ Da. If the molecular weight of the chitooligosaccharide is lower than $0.5 \times 10^3$ Da, this may result in problems in terms of anti-adhesion effects. On the other hand, if the molecular weight of the chitooligosaccharide is higher than $1.0 \times 10^4$, this may result in limitations of in vivo applications.

The content of the chitooligosaccharide is in a range of about 0.05% by weight to about 15% by weight, and preferably about 0.1% by weight to about 10% by weight, based on the total weight of the composition of the present invention. If the content of the chitooligosaccharide is lower than 0.05% by weight, this may result in problems in terms of anti-adhesion effects. On the other hand, if the content of the chitooligosaccharide is higher than 15% by weight, this may result in problems in terms of production due to solubility.

The composition of the present invention may be formulated into a variety of dosage forms, preferably a solution, gel, or the like. The solution or gel may be prepared with the addition of pharmaceutically acceptable excipients, additives or the like. For example, physiological saline or distilled water may be used.

The product including the composition of the present invention may be used according to the following general method, for the purpose of preventing post-operative adhesions between tissues or organs.

1) Confirm to make complete hemostasis at lesions or surgical regions.

2) Ensure that the present product is unpacked in a sterile place, a syringe is decapped and a catheter is then turned to be fixed thereto.

3) The composition is sufficiently applied to the target site. If necessary, auxiliary means, such as spray, may be used to achieve effective application of the solution.

4) The residual solution after administration is discarded.

An effective amount of the composition in accordance with the present invention may be preferably in a range of about 0.01 to about 10 ml/unit area (1 cm$^2$), and more preferably about 0.1 to 5 ml. The effective amount of the composition may vary depending on various factors, such as depth, size and location of lesions or surgical regions, tissue and organ specificity of wounded regions, dose of the composition of the present invention, and personal opinion of surgical operator.

Advantageous Effects

As described above, the composition for preventing adhesion in accordance with the present invention is capable of minimizing a foreign-body reaction through the use of a bio-derived material which is free from chemical crosslinking, undergoes in vivo retention for a certain period of time, followed by decomposition and absorption, does not interfere with healing of wounds following surgical operations, can be conveniently used upon application thereof, and is capable of preventing adhesions.

MODE FOR INVENTION

These and other objects, advantages and features of the present invention and methods of achieving the same will become apparent from the detailed embodiments given below which are made in conjunction with the following drawings. This invention may, however, be embodied in different forms and should not be construed as being limited to the embodiments set forth herein. Rather, these embodiments are provided so that this disclosure will be thorough and complete, and will fully convey the scope of the invention to those skilled in the art. Therefore, the present invention should be defined by attached claims only.

Comparative Examples 1 to 4

Preparation of Control Group and Composition for Preventing Adhesion of Hyaluronic Acid Alone Comparative Example 1

Guardix-Sol

As an anti-adhesion agent made up of hyaluronic acid (HA) and carboxymethyl cellulose, a commercially available product (Guardix-sol, manufactured by BIORANE CO., LTD., Korea) was used.

Comparative Example 2

HA having a molecular weight of $2.5 \times 10^6$ to $3 \times 10^6$ Da and a viscosity of 30 dl/g to 35 dl/g was dissolved to a concentration of 0.5% by weight in physiological saline. The resulting aqueous solution was dissolved in a cold chamber at 4° C. for about 2 days, thereby obtaining an HA-including gel composition.

Comparative Example 3

An HA-including gel composition was obtained in the same manner as in Example 1, except that HA was dissolved to a concentration of 1% by weight in physiological saline.

Comparative Example 4

Hetastarch (HES, 670/0.75) was dissolved to a concentration of 8.0% by weight in physiological saline, thereby obtaining a composition of HES alone.

Examples 1 to 5

Preparation of Composition for Preventing Adhesion Including Hyaluronic Acid and Hetastarch 450/0.7

Example 1

A 6% HES (450/0.7) solution was dissolved to a concentration of 0.03% by weight in physiological saline, and HA having a molecular weight of $2.5 \times 10^6$ to $3 \times 10^6$ Da and a viscosity of 30 dl/g to 35 dl/g was dissolved to a concentration of 1% by weight in the obtained physiological saline solution. The resulting aqueous solution was dissolved in a cold chamber at 4° C. for about 2 days, thereby obtaining a gel composition including HA and HES.

Example 2

A gel composition including HA and HES was obtained in the same manner as in Example 1, except that HES was dissolved to a concentration of 0.06% by weight in physiological saline.

Example 3

A gel composition including HA and HES was obtained in the same manner as in Example 1, except that HES was dissolved to a concentration of 0.12% by weight in physiological saline.

Example 4

A gel composition including HA and HES was obtained in the same manner as in Example 1, except that HES was dissolved to a concentration of 0.24% by weight in physiological saline.

Example 5

A gel composition including HA and HES was obtained in the same manner as in Example 1, except that HES was dissolved to a concentration of 0.5% by weight in physiological saline.

Example 6

Preparation of Composition for Preventing Adhesion Including Hyaluronic Acid and Hetastarch 670/0.75

A gel composition including HA and HES was obtained in the same manner as in Example 1, except that a 6% HES (670/0.75) solution having different molecular weight and molar substitution degree was dissolved to a concentration of 0.5% by weight in physiological saline.

Example 7

Preparation of Composition for Preventing Adhesion Including Hyaluronic Acid and Hetastarch 264/0.45

A gel composition including HA and HES was obtained in the same manner as in Example 1, except that a 10% HES (264/0.45) solution having different molecular weight and molar substitution degree was dissolved to a concentration of 0.5% by weight in physiological saline.

Example 8

Preparation of Composition for Preventing Adhesion Including Hyaluronic Acid and Chitooligosaccharide Chitooligosaccharide having a molecular weight of $1 \times 10^3$ to $5 \times 10^3$ Da (hereinafter, referred to as "COS", manufactured by KITTOLIFE CO., LTD., Korea) was dissolved to a concentration of 0.5% by weight in physiological saline and HA was dissolved to be 1% by weight of the solution. The resulting aqueous solution was dissolved in a cold chamber at 4° C. for about 2 days, thereby obtaining a gel composition including HA and COS.

Experimental Example 1

Anti-Adhesion Test in Rat Cecal-Abdominal Wall Abrasion Model

Anti-tissue adhesion performance of the samples prepared in Comparative Examples 1 to 4 and Examples 1 to 8 was evaluated using a rat cecal-abdominal wall abrasion model. As experimental animals, 7-week old Sprague-Dawley male rats (SLC, Japan) were used and grouped (n=5/group). For induction of adhesions, experimental animals were anesthetized by peritoneal administration of Ketamin•HCl (0.1 ml/100 g), followed by abdominal shaving and disinfection with 70% ethanol, and a 4 to 5 cm incision was then made on the midline at abdominal region. The cecum was taken out of the incised part, and the serous membrane of the cecum (1.2 cm×1.2 cm) was rubbed with a sterilized gauze until hemorrhage occurred, and the opposite abdominal lining (1.2 cm×1.2 cm) was traumatized using a reagent spoon. Two spots 1 cm away from the rubbing-injured regions were fixed by a 5-0 nylon suture such that two injured surfaces were brought into contact, thus promoting the formation of adhesions.

Figure 1:
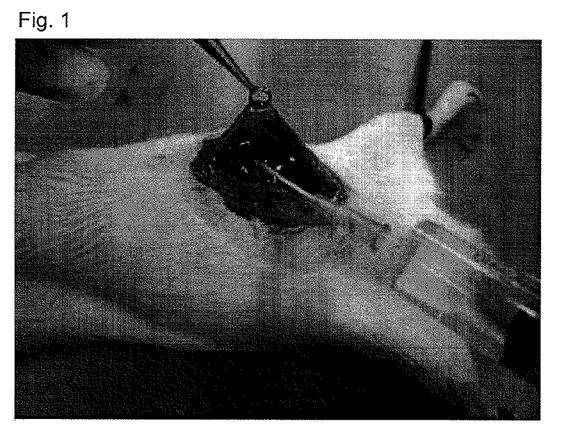
FIG. 1 is a photograph showing administration of the composition according to the examples of the present invention to an animal.

A negative control group was infused with physiological saline. For an experimental group, 5 ml of an anti-adhesion solution was infused into each of the injured regions (see FIG. 1). Then, the abdominal lining and skin were sutured. After surgeries were completed, animals were fed a diet and water ad libitum for one week and were sacrificed, followed by evaluation of adhesions. Using an adhesion evaluation system, scores obtained were summed up and averaged (*Am. J. Obstet. Gynecol.*, 146, 88-92, 1983). The results are given in Table 1 to Table 4, respectively.

The adhesion extent was evaluated according to the following criteria on a scale of 0 to 5 (0: No adhesions, 1: One thin film-like adhesion, 2: Two or more thin film-like adhesions, 3: Focal localized thick adhesions, 4: Plate-like localized adhesions, 5: Very thick adhesions with formation of blood vessels or one or more plate-like dense adhesions).

The adhesion strength was evaluated according to the following criteria on a scale of 1 to 4 (1: film-like adhesion which is easily releasable by very weak force, 2: adhesion which requires moderate force to release the adhesion, 3: Adhesion which is releasable with application of considerable pressure, 4: Very strong adhesion difficult to release or requiring very high pressure to release the adhesion).

TABLE 1

Administration of composition for preventing adhesion including hyaluronic acid

| | Adhesion extent | Adhesion strength | Adhesion area (cm²) | Adhesion area decrease rate (%) |
|---|---|---|---|---|
| Control | 3.88 ± 0.35 | 2.88 ± 0.35 | 1.36 ± 0.25 | 0 |
| Comparative Example 1 | 3.20 ± 0.45 | 2.60 ± 0.55 | 0.78 ± 0.12** | 42.7 |
| Comparative Example 2 | 3.25 ± 0.50* | 2.75 ± 0.50* | 0.80 ± 0.13** | 40.5 |
| Comparative Example 3 | 3.10 ± 0.58* | 2.55 ± 0.50 | 0.66 ± 0.17** | 51.3 |
| Comparative Example 4 | 3.80 ± 0.45 | 2.80 ± 0.45 | 1.20 ± 0.11 | 11.7 |

Data were represented by mean ± S.D(n = 5)
*p < 0.05 versus None (negative control),
**p < 0.05 versus None (negative control)

As shown in Table 1 above, Comparative Examples 2 and 3 exhibited a reduction of tissue adhesions as compared to the control group, and Comparative Example 3 exhibited increased anti-adhesion effects as compared to Comparative Example 2. Therefore, it was demonstrated that the composition of HA alone has superior anti-adhesion effects as compared to the conventional commercially available composition.

It can be seen that the composition of Comparative Example 4 has very poor anti-adhesion effects. Therefore, it seems that HES alone is insufficient to serve as a barrier.

Figure 2:
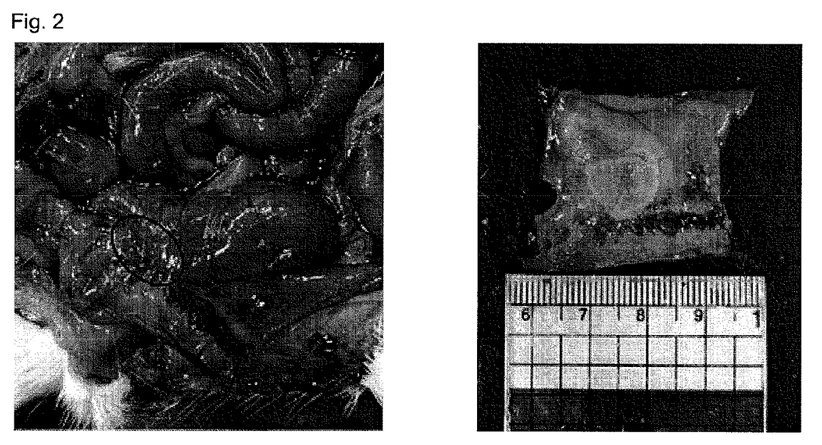
FIG. 2 is a representative photograph showing the results of an animal experiment according to the control group of the present invention.
Figure 3:
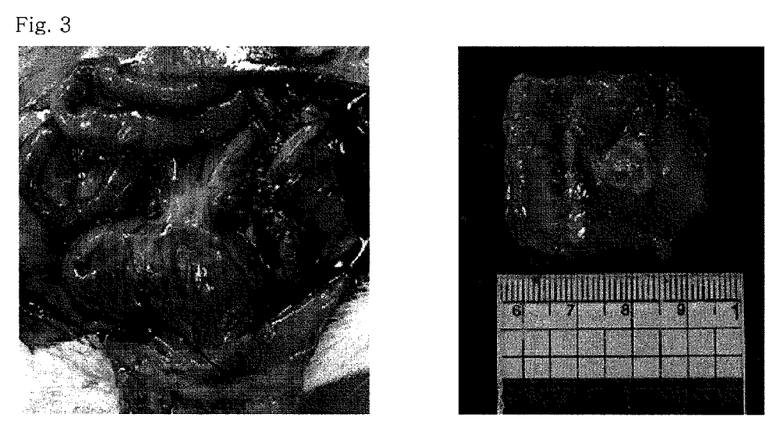
FIG. 3 is a representative photograph showing the results of an animal experiment according to the comparative examples of the present invention.
Figure 4:
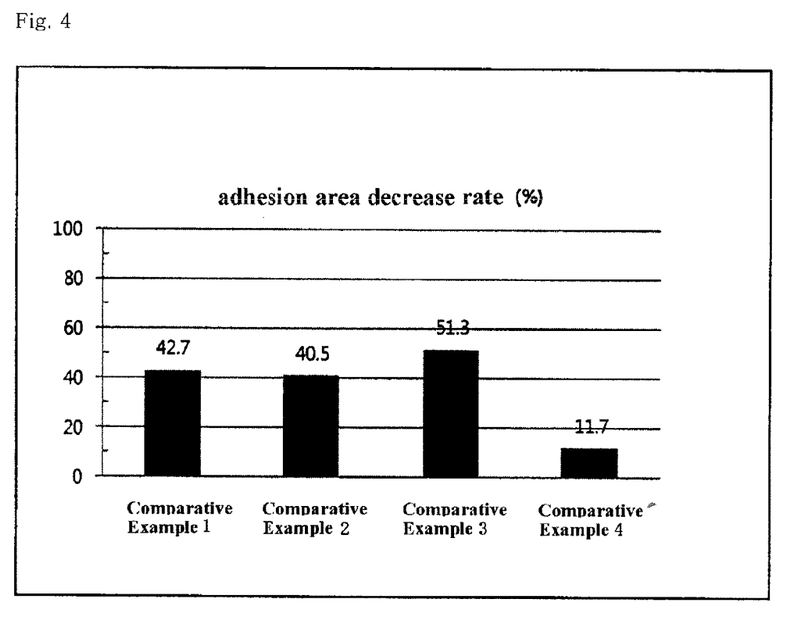
FIG. 4 and FIG. 10 are graphs showing the comparative results of adhesion area decrease rate (%) in an animal experiment of the composition in accordance with the present invention.

The representative photograph for the animal experiment results of the control group is shown in FIG. 2; the representative photograph for the animal experiment results of Comparative Example 1 is shown in FIG. 3; and a decrease rate (%) of tissue adhesion area in the animal experiments is graphically shown in FIG. 4.

TABLE 2

Administration of composition for preventing adhesion including hyaluronic acid and hetastarch 450/0.7

| | Adhesion extent | Adhesion strength | Adhesion area (cm²) | Adhesion area decrease rate (%) |
|---|---|---|---|---|
| Control | 3.73 ± 0.46 | 3.00 ± 0.00 | 0.80 ± 0.16 | 0 |
| Example 1 | 1.75 ± 1.26* | 1.25 ± 0.96** | 0.26 ± 0.09** | 67.5 |
| Example 2 | 1.60 ± 1.14** | 1.20 ± 0.84** | 0.16 ± 0.08** | 80.0 |
| Example 3 | 1.60 ± 1.14** | 1.20 ± 0.84** | 0.12 ± 0.12** | 85.0 |
| Example 4 | 1.40 ± 1.14** | 1.20 ± 0.84** | 0.07 ± 0.11** | 91.1 |
| Example 5 | 1.20 ± 1.30** | 0.80 ± 0.84** | 0.06 ± 0.10** | 92.5 |

Data were represented by mean ± S.D(n = 5)
*p < 0.05 versus None (negative control),
**p < 0.05 versus None (negative control)

As shown in Table 2 above, it was demonstrated that the groups to which the compositions of Example 1 to Example 5 were administered exhibited a remarkable reduction of tissue adhesions as compared to the control group, and when the content (in terms of % by weight) of HES in the example compositions of the present invention is increased, the adhesion area is decreased and the anti-tissue adhesion performance is superior.

Figure 5:
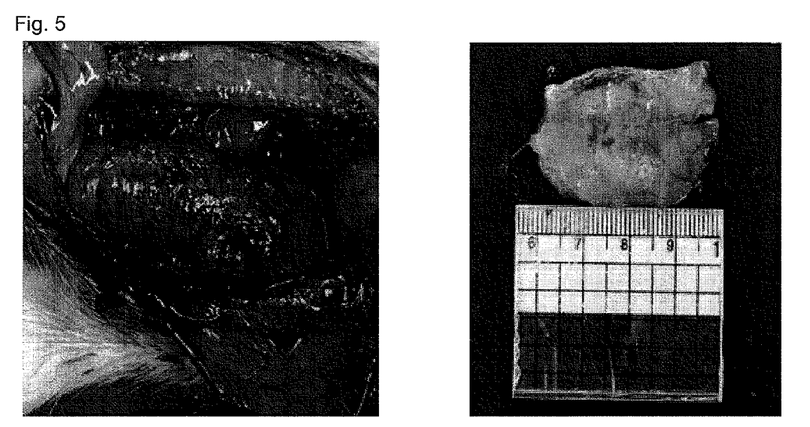
FIG. 5 and FIG. 6 are representative photographs showing the results of an animal experiment according to the examples of the present invention.
Figure 6:
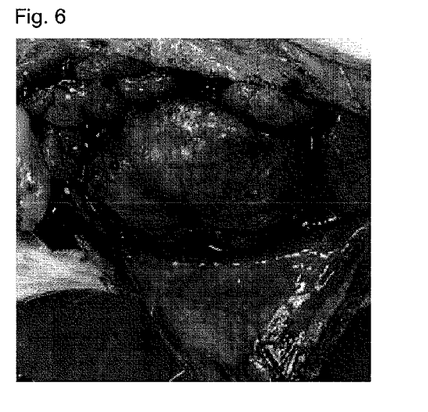
Figure 7:
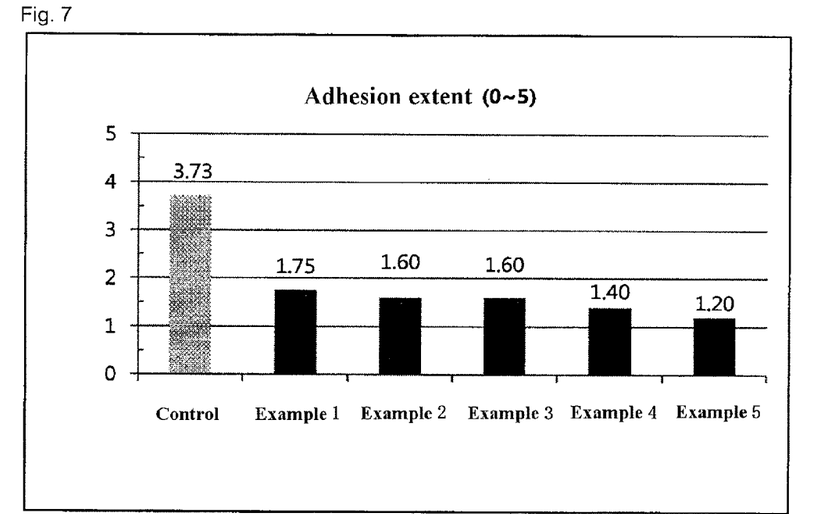
FIG. 7 is a graph showing the comparative results of adhesion extent in an animal experiment of the composition in accordance with the present invention.
Figure 8:
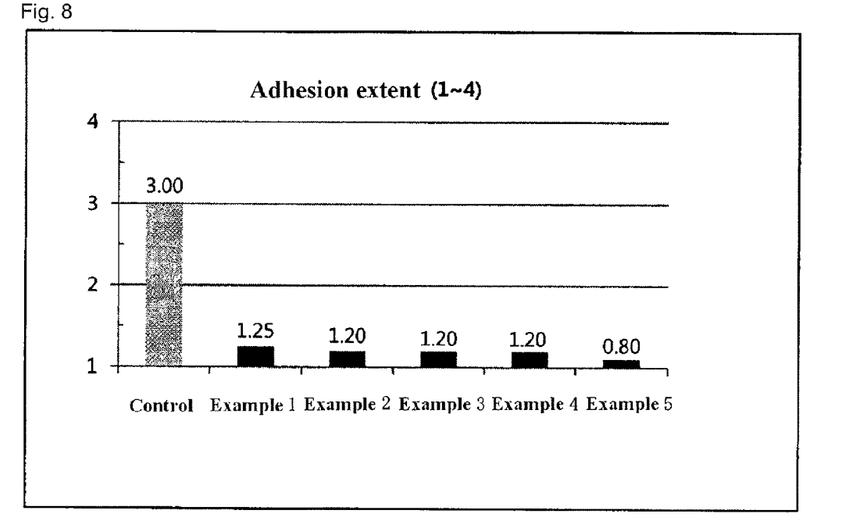
FIG. 8 is a graph showing the comparative results of adhesion strength in an animal experiment of the composition in accordance with the present invention.
Figure 9:
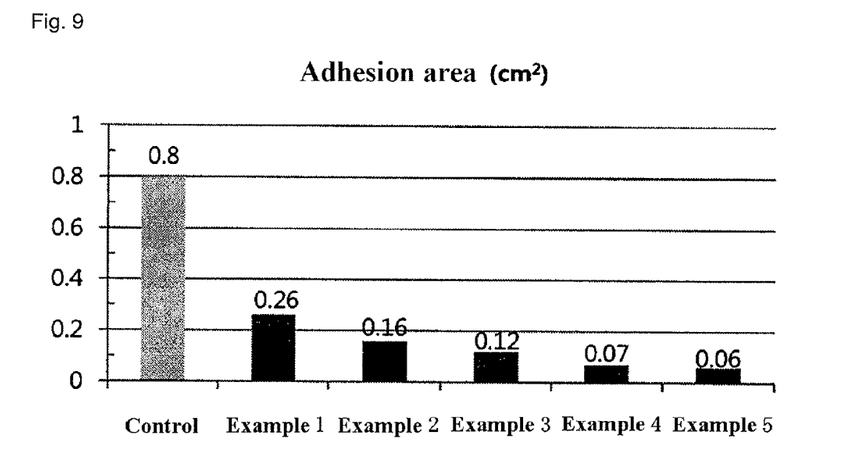
FIG. 9 is a graph showing the comparative results of adhesion area in an animal experiment of the composition in accordance with the present invention.
Figure 10:
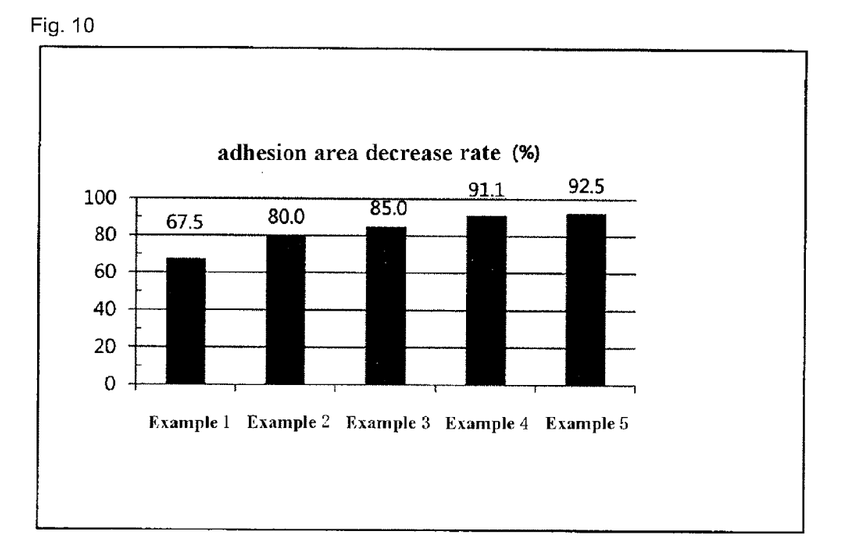

The animal experiment results of Example 5 are shown in FIG. 5; a representative photograph for the results without occurrence of adhesions (one case in Example 5-treated group) is shown in FIG. 6; and the tissue adhesion extent, adhesion strength, adhesion area, and adhesion area decrease rate (%) in the animal experiments are shown in FIGS. 7 to 10, respectively.

TABLE 3

Administration of composition for preventing adhesion including hyaluronic acid and hetastarch 670/0.75 or 264/0.45

|  | Adhesion extent | Adhesion strength | Adhesion area (cm$^2$) | Adhesion area decrease rate (%) |
|---|---|---|---|---|
| Control | 3.60 ± 0.55 | 3.00 ± 0.00 | 0.73 ± 0.07 | 0 |
| Example 6 | 2.00 ± 0.71** | 1.80 ± 0.45** | 0.11 ± 0.16** | 84.9 |
| Example 7 | 1.80 ± 1.30* | 1.20 ± 0.84** | 0.18 ± 0.18** | 75.4 |

Data were represented by mean ± S.D(n = 5)
*p < 0.05 versus None (negative control),
**p < 0.05 versus None (negative control)

As shown in Table 3 above, it was demonstrated that Examples 6 and 7 exhibited a reduction of tissue adhesions as compared to the control group. Example 6 in which 0.5% by weight of a 10% HES (670/0.75) solution was added to the gel composition exhibited a greater reduction of the adhesion area, as compared to Example 7 in which 0.5% by weight of a 6% HES (264/0.45) solution was added to the gel composition. In addition, no occurrence of adhesions was observed in two animals of Example 6, thus showing superior inhibition of adhesion.

TABLE 4

Administration of composition for preventing adhesion including hyaluronic acid and chitooligosaccharide

|  | Adhesion extent | Adhesion strength | Adhesion area (cm$^2$) | Adhesion area decrease rate (%) |
|---|---|---|---|---|
| Control | 3.60 ± 0.55 | 3.00 ± 0.00 | 0.72 ± 0.11 | 0 |
| Example 8 | 2.25 ± 1.50 | 1.50 ± 1.00* | 0.27 ± 0.18** | 62.5 |

Data were represented by mean ± S.D (n = 5)
*p < 0.05 versus None (negative control),
**p < 0.05 versus None (negative control)

As shown in Table 4 above, it was demonstrated that Example 8 with the addition of COS exhibited a greater reduction of tissue adhesions, as compared to the control group.

When administered, all of the experimental groups 1 to 8 exhibited no particular inflammatory responses due to the applied materials, as compared to the control group, and therefore it was also demonstrated that the applied materials have excellent biocompatibility.

What is claimed is:

1. A composition for reducing adhesion comprising a hyaluronic acid and, a hydroxyethyl starch, wherein the hyaluronic acid has a molecular weight of about $5.0 \times 10^5$ to about $3 \times 10^6$ Da, a content of the hyaluronic acid is in a range of about 0.3% to about 7.0% by weight, based on a total weight of the composition, the hydroxyethyl starch has a molecular weight of about $2.0 \times 10^5$ to about $1.0 \times 10^6$ Da and a molar substitution degree of about 0.2 to about 0.8, and a content of the hydroxyethyl starch is in a range of about 0.1% by weight to about 2.0% by weight, based on a total weight of the composition.

2. The composition according to claim 1, wherein the hyaluronic acid has a molecular weight of $0.8 \times 10^6$ to $3 \times 10^6$ Da.

3. The composition according to claim 1, wherein the content of the hyaluronic acid is in the range of 0.5 to 5.0% by weight, based on the total weight of the composition.

4. The composition according to claim 1, wherein the hydroxyethyl starch has a molar substitution degree of 0.75 to 0.4.

5. The composition according to claim 1, wherein the hydroxyethyl starch has a molecular weight of $2.5 \times 10^5$ to $6.7 \times 10^5$ Da and a molar substitution degree of 0.75 to 0.4.

6. The composition according to claim 1, wherein the hyaluronic acid is extracted from an animal tissue or prepared by a fermentation method.

7. A method for reducing a post-operative adhesion of surrounding organs or tissues, comprising administering a composition of claim 1 to a mammal.

8. A method for reducing a post-operative adhesion of surrounding organs or tissues, comprising administering a composition of claim 2 to a mammal.

9. A method for reducing a post-operative adhesion of surrounding organs or tissues, comprising administering a composition of claim 3 to a mammal.

10. A method for reducing a post-operative adhesion of surrounding organs or tissues, comprising administering a composition of claim 4 to a mammal.

11. A method for reducing a post-operative adhesion of surrounding organs or tissues, comprising administering a composition of claim 5 to a mammal.

12. A method for reducing a post-operative adhesion of surrounding organs or tissues, comprising administering a composition of claim 6 to a mammal.

13. The method according to claim 7, wherein the mammal is human.

14. A composition for reducing adhesion comprising a hyaluronic acid and a hydroxyethyl starch, wherein the hyaluronic acid has a molecular weight of $5.0 \times 10^5$ to $3 \times 10^6$ Da, a content of the hyaluronic acid is in a range of 0.3 to 7.0% by weight, based on a total weight of the composition, the hydroxyethyl starch has a molecular weight of $2.0 \times 10^5$ to $1.0 \times 10^6$ Da and a molar substitution degree of 0.2 to 0.8, and a content of the hydroxyethyl starch is in a range of about 0.06% by weight to about 0.5% by weight, based on a total weight of the composition.

15. The composition according to claim 14, wherein the hyaluronic acid has a molecular weight of $0.8 \times 10^6$ to $3 \times 10^6$ Da.

16. The composition according to claim 14, wherein the content of the hyaluronic acid is in the range of 0.5 to 5.0% by weight, based on the total weight of the composition.

17. The composition according to claim 14, wherein the hydroxyethyl starch has a molar substitution degree of 0.75 to 0.4.

18. A method for reducing a post-operative adhesion of surrounding organs or tissues, comprising administering a composition of claim 14 to a mammal.

19. A method for reducing a post-operative adhesion of surrounding organs or tissues, comprising administering a composition of claim 15 to a mammal.

20. A method for reducing a post-operative adhesion of surrounding organs or tissues, comprising administering a composition of claim 16 to a mammal.

21. A method for reducing a post-operative adhesion of surrounding organs or tissues, comprising administering a composition of claim 17 to a mammal.

22. The method according to claim 18, wherein the mammal is human.

* * * * *

UNITED STATES PATENT AND TRADEMARK OFFICE
CERTIFICATE OF CORRECTION

| | | |
|---|---|---|
| PATENT NO. | : 8,703,740 B2 | Page 1 of 1 |
| APPLICATION NO. | : 13/131996 | |
| DATED | : April 22, 2014 | |
| INVENTOR(S) | : H. Cho et al. | |

It is certified that error appears in the above-identified patent and that said Letters Patent is hereby corrected as shown below:

Title Page 2, References Cited/Other Publications, column 2, line 10, please change "Med. Oin. North" to -- Med. Clin. North --

Signed and Sealed this
Third Day of March, 2015

Michelle K. Lee
*Deputy Director of the United States Patent and Trademark Office*